(12) United States Patent
Martin

(10) Patent No.: US 6,586,758 B2
(45) Date of Patent: Jul. 1, 2003

(54) RADIOPHARMACEUTICAL PIG AND TRANSPORTATION APPARATUS

(75) Inventor: Matthew R. Martin, Remsenburg, NY (US)

(73) Assignee: Biodex Medical Systems, Inc., Shirley, NY (US)

( * ) Notice: Subject to any disclaimer, the term of this patent is extended or adjusted under 35 U.S.C. 154(b) by 215 days.

(21) Appl. No.: 09/878,502

(22) Filed: Jun. 11, 2001

(65) Prior Publication Data
US 2002/0195575 A1 Dec. 26, 2002

(51) Int. Cl.⁷ .................. G21F 5/00; G21F 5/015; G21F 5/018; G21F 5/06; G21F 5/14
(52) U.S. Cl. .................. 250/515.1; 250/506.1; 250/507.1; 29/428; 29/469; 976/DIG. 350; 976/DIG. 351; 600/5
(58) Field of Search .................. 250/505.1, 506.1, 250/507.1, 515.1; 29/469, 428; 976/DIG. 351, DIG. 350; 600/5

(56) References Cited

U.S. PATENT DOCUMENTS 5,519,931 A * 5/1996 Reich .................. 250/507.1
6,425,174 B1 * 7/2002 Reich .................. 250/507.1

* cited by examiner

Primary Examiner—Huan Tran
(74) Attorney, Agent, or Firm—Gibbons, Del Deo, Dolan, Griffinger & Vecchione

(57) ABSTRACT

An apparatus and method for transporting radiopharmaceutical substances. The apparatus comprises a radiation shielding pig having an elongated sidewall that extends between two ends and that defines an elongated, interior chamber. The sidewall is thinner than each of the ends. A radiation shield defines at least one cavity. The shield has two open ends and a central area between the open ends that is thicker than each of the two open ends. Also, a method of assembling and disassembling the apparatus includes, placing a syringe filled with a radiopharmaceutical substance into the pig; placing the pig containing the filled syringe in the radiation shield; placing the pig and the shield into an ammunition can for transporting the radioactive substance contained in the syringe.

21 Claims, 8 Drawing Sheets

RADIOPHARMACEUTICAL PIG AND TRANSPORTATION APPARATUS

STATEMENT REGARDING FEDERALLY SPONSORED RESEARCH OR DEVELOPMENT

Not Applicable.

BACKGROUND OF THE INVENTION

1. Field of the Invention

The present invention generally relates to a radiopharmaceutical pig and apparatus for transporting radioactive substances, specifically radiopharmaceuticals.

2. Discussion of Related Art

Generally, radioactive drugs are in a liquid form suitable for injection into a patient. Because of the radioactive characteristics of these drugs, they must be handled according to regulations promulgated by various departments of the United States government, including the Department of Transportation (DOT), the Nuclear Regulatory Commission, and the Occupational Health and Safety Administration (collectively "federal regulation"). Federal regulation guidelines presently require that a radioactivity reading on the outside surface of a shipping container housing radioactive substances be less than 50 mRems/hour and a reading taken at a distance of 1 meter from the outside surface of the container should be less than 1 mRems/hour in order for the container with the radioactive substance to be classified as a Yellow-II package. It is desirable to have packages conform to Yellow-II package guidelines.

In the nuclear medicine and radiopharmaceutical industries, radioactive drugs are used for various applications, including the internal imaging of various human organs for diagnostic purposes. Among the various modalities of internal radioactive imaging, Positron Emission Tomography (PET) is a relatively recent imaging method that falls within the sphere of nuclear medicine. Nuclear medicine is an imaging modality in which radioactive material is injected into a patient rather than using an external radioactive source. Whereas traditional diagnostic techniques such as X-rays, computerized tomography scans, or magnetic resonance imaging produce static images of the body's anatomy or structure, PET is a diagnostic imaging technology used to measure metabolic human cell activity. In this manner, cancer cells can be visualized before they are large enough to be detected as a structure. Additionally, PET imaging can identify cancerous structures prior to surgery. PET is used not only to diagnose and manage patients with cancer but also is used for patients with neurological disorders and heart disease.

Fluorodeoxyglucose tagged with Fluorine-18 as a marker ("FDG F18") is the most common short-lived radiopharmaceutical substance used in PET. Because FDG F18 allows accurate and precise diagnoses of tumors at their early stages, it is considered to be the solution of choice for the diagnosis of cancer and for monitoring a patient's response to cancer treatment.

FDG F18 is injected into the patient and through the natural metabolic differentiation in absorption allows cancerous tissues to be identified because cancerous tissue has a higher metabolic rate than that of surrounding healthy tissue.

FDG F18 has a high radioactive energy with about a two hour half life. A single dose of FDG F18 usually requires up to 15 millicuries (mCi) of FDG F18. Thus, if a shipment of FDG F18 will be administered into a patient by a nuclear medical facility ten hours after its shipment from the radiopharmaceutical manufacturer, an initial dose of about 480 mCi must be shipped. Radiopharmaceutical manufacturers however, desire systems that could accommodate initial doses as high as about 700 mCi FDG F18.

One type of delivery container currently used for the delivery of syringes containing radioactive drugs is known as a radiopharmaceutical pig. The radiopharmaceutical pig typically includes a two-part assembly and has an inner chamber suitable for carrying a syringe. The chamber is lined with a radiation shielding material, usually elemental lead, although other materials such as tungsten have been used. The exterior of the radiopharmaceutical pig is generally a shell made out of polystyrene, polypropylene, metal or other suitable materials well known to one skilled in the art. The pig is then placed into a cylindrical sealed lead enclosure.

One such device is presently manufactured by Biodex Medical Systems, Inc. This apparatus includes a pig wherein the thicknesses of the pig's wall, upper and lower portions contain approximately ½" lead. A syringe containing a radiopharmaceutical substance is placed inside the pig. The pig is then placed in another sealed cylindrical lead enclosure which is located within a polyethylene shipping container to meet federal requirements for a maximum radioactivity level detectable at the outside of the container surface not to exceed 50 mRems/hour. With this apparatus, the total weight of the pig with the syringe and cylindrical lead enclosure, reaches about 50 lbs. for radioactive doses of up to about 95 mCi. This is considered the maximum desirable weight for shipping and handling, for preventing possible injury to persons handling the shipping container and for limiting shipping costs. If greater initial doses are required, the combined weight of the pig, the lead enclosure and syringe exceeds 50 lbs. because a heavier pig containing thicker lead is used to provide the required shielding from radioactivity. This weight exceeds the acceptable and desirable levels for the reasons specified above. Thus, because of the ever increasing pressure to reduce medical costs, an inexpensive pig would be beneficial to the health care system and would also ultimately benefit the recipients of such radiopharmaceutical medical treatments.

There are pigs and cylindrical lead enclosures available today that can accommodate up to three syringes, each syringe containing a single dose, in a single pig. The problem with these pigs and enclosures is that there is significant radioactivity hand exposure. When the top lid of one of the lead enclosures is opened, the pig exposes the radioactive substances in each of the syringes. Because all three doses are housed in a single pig.

Accordingly, there is a need for a lightweight, radiopharmaceutical transportation apparatus that weighs less than 50 lbs. and also limits an amount of radioactivity that penetrates to the surface of the apparatus so that the amount of radioactivity detectable on the outside surface of the apparatus is less than about 50 mRems/hour. There is a further need for a radiopharmaceutical transportation apparatus that accommodates multiple doses of radioactive substances, weighs less than about 50 lbs. and adequately shields against radioactivity including radioactivity exposure to the hands when the container is opened. There is also a need for a radiopharmaceutical transportation apparatus that can hold up to 700 mCi of a radioactive substance, weighs less than 50 lbs. and still limits an amount of radioactivity penetrating the outside surface of the apparatus to a level of radioactivity less than 50 mRems/hour.

BRIEF SUMMARY OF THE INVENTION

An aspect of the present invention resides in an improved pig and radiation shield for transporting radioactive substances. The pig has an elongated sidewall between two closed ends. The two closed ends are thicker than the sidewall and contain greater amounts of lead shielding. The pig defines a chamber bounded by the sidewall and closed ends. The pig separates into two halves to that when separated, a syringe containing a radioactive substance may be inserted into the chamber. The two halves of the pig are then closed to seal the syringe within the chamber. The radiation shield is elongated and open at its two ends to define a cavity, into which is placed the pig. The two closed ends of the pig may protrude through both open ends of the radiation shield simultaneously or they could be even with the open ends or fall short of reaching the open ends. The combination of shielding of the pig and shielding of the radioactive shield provide sufficient radiation penetration resistance so that Yellow-II package guidelines are met.

DESCRIPTION OF THE PREFERRED EMBODIMENT

The invention provides a radiopharmaceutical pig ("pig") and transportation apparatus, which is lighter and more efficient that conventional pigs and transportation apparatus.

Figure 1:
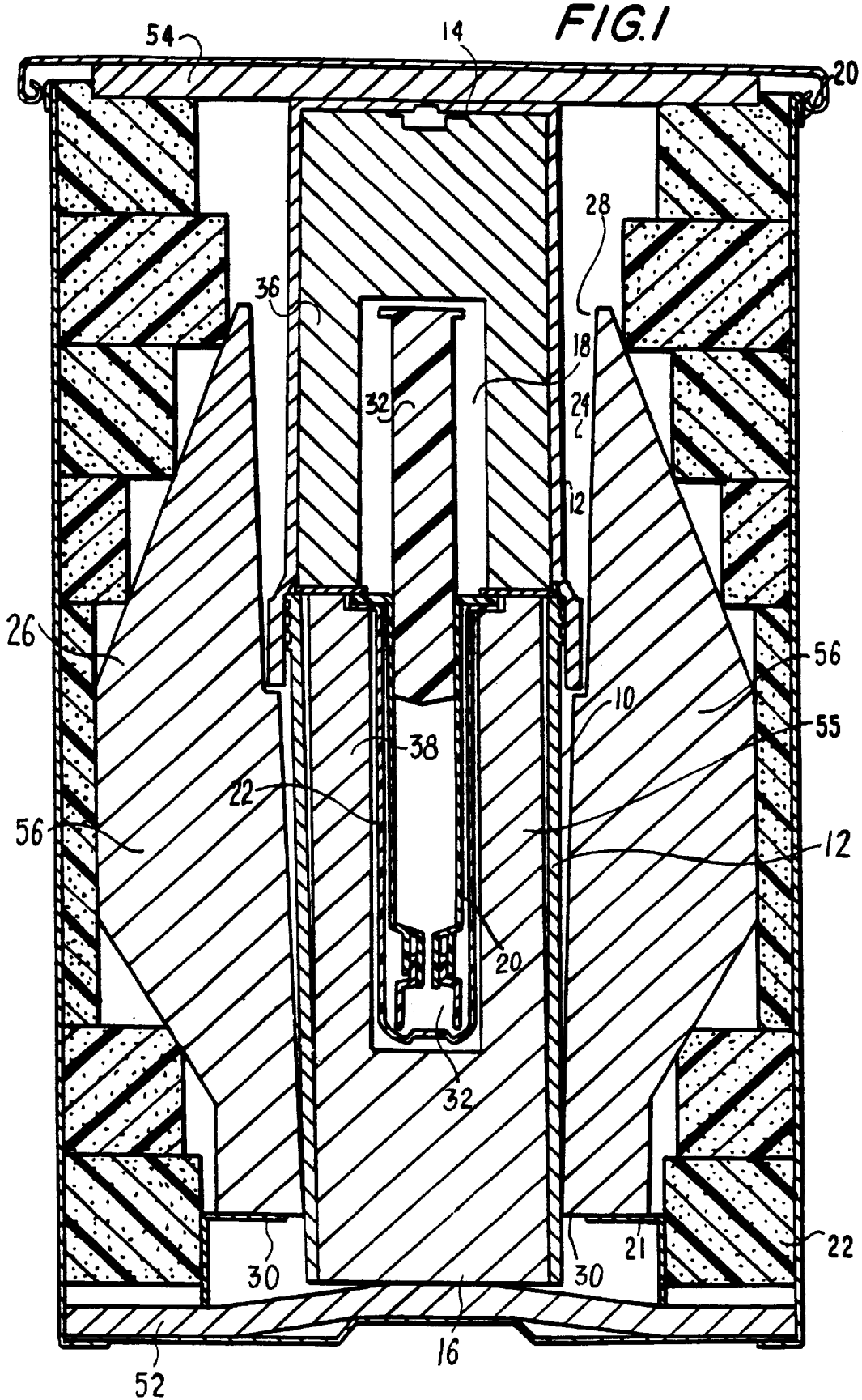
FIG. 1 shows a cross-section of the radiopharmaceutical pig and transportation apparatus in accordance with a first embodiment of the invention.

Turning to FIG. 1, the pig 10 of the present invention has an elongated tubular sidewall 12 that extends between two closed ends 14, 16. The two closed ends 14, 16 are thicker and contain relatively more radiation shielding material than is contained in the elongated tubular sidewall 12. The two closed ends 14, 16 and side wall 12 form an interior chamber 18 to house a radioactive substance which may be contained within a syringe 20. The pig 10 also has a plastic liner 22 fitted inside the chamber 18 for protecting the syringe inside the pig 10.

The radioactive resistant material used to make the pig 10 may be lead, whose thickness at the two closed ends 14, 16 sufficiently shields against penetration of radiation through the closed ends 14, 16 and whose thickness at the elongated tubular sidewall 12 itself may not be sufficient to provide adequate shielding against penetration of radiation from the radioactive substances inside the pig 10. To compensate for this radiation shielding deficiency in the sidewall 12 of the pig 10, the pig 10 is fitted within a cavity 24 defined by a radiation shield 26, whose thickness in addition to the thickness of the sidewall 12 of the pig 10 is sufficient to resist penetration of radiation, preferably by an amount at least as great as the amount of radiation penetration resistance provided by the closed ends 14, 16.

Although the radiation shield 26 is required for resisting radiation penetration with respect to the elongated tubular sidewall 12, the radiation shield 26 can be configured with open ends 28, 30 because the lead at the two closed ends 14, 16 of the pig 10 is sufficient to provide the necessary shielding above and below the radioactive source inside the syringe 32. This aspect allows the closed ends 14, 16 of the pig 10 to extend beyond each of the open ends 28,30 of the radiation shield 26, which provides for a combination pig 10 and radiation shield 26 that is relatively lightweight. The pig 10 is preferably configured as an assembly of two sections wherein the two sections are selectively mated with each other for closing the pig through a threading configuration or any other suitable method of mating the two sections (e.g., clasp, tong and groove, etc.).

Figure 2:
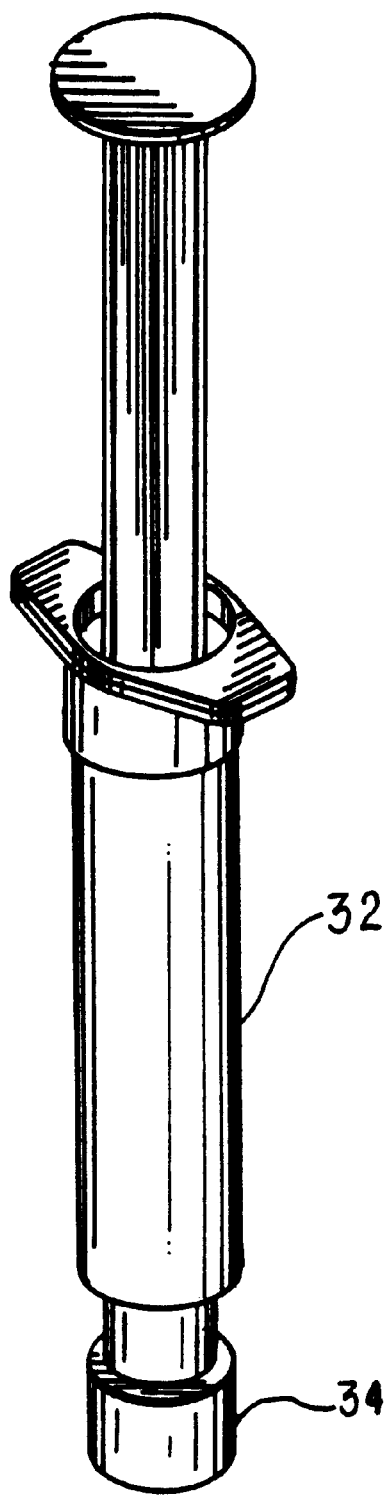
FIG. 2 is a perspective view of a conventional syringe with a luer lock.
Figure 3:
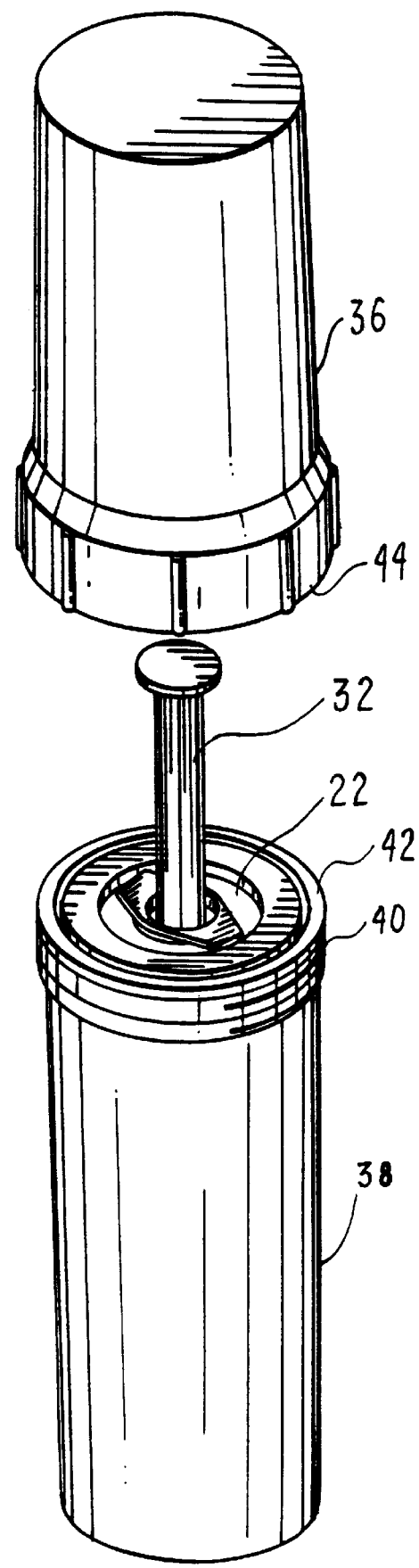
FIG. 3 is an elevational view of the radiopharmaceutical pig of FIG. 1 having two mateable sections, with the conventional syringe of FIG. 2 arranged inside one of the two sections.

FIG. 2 shows the conventional 5 cc syringe 32 filled to capacity and closed with a luer lock 34. A luer lock 34 is often used by radiopharmaceutical manufacturers producing FDG F18 as a safety measure to prevent leakage. This is particularly important when air shipping the FDG F18 because the closed syringe must be able to withstand varied air pressures. The syringe 32 resides in the plastic liner 22 of the pig 10 (FIG. 3). As shown in FIG. 3, the pig 10 has two sections 36, 38 that mate with each other via a thread configuration 40. The thread configuration 40 is at the outside of inner end 42 of the section 38 at the inside of widened lip 44 of the section 36.

Figure 4:
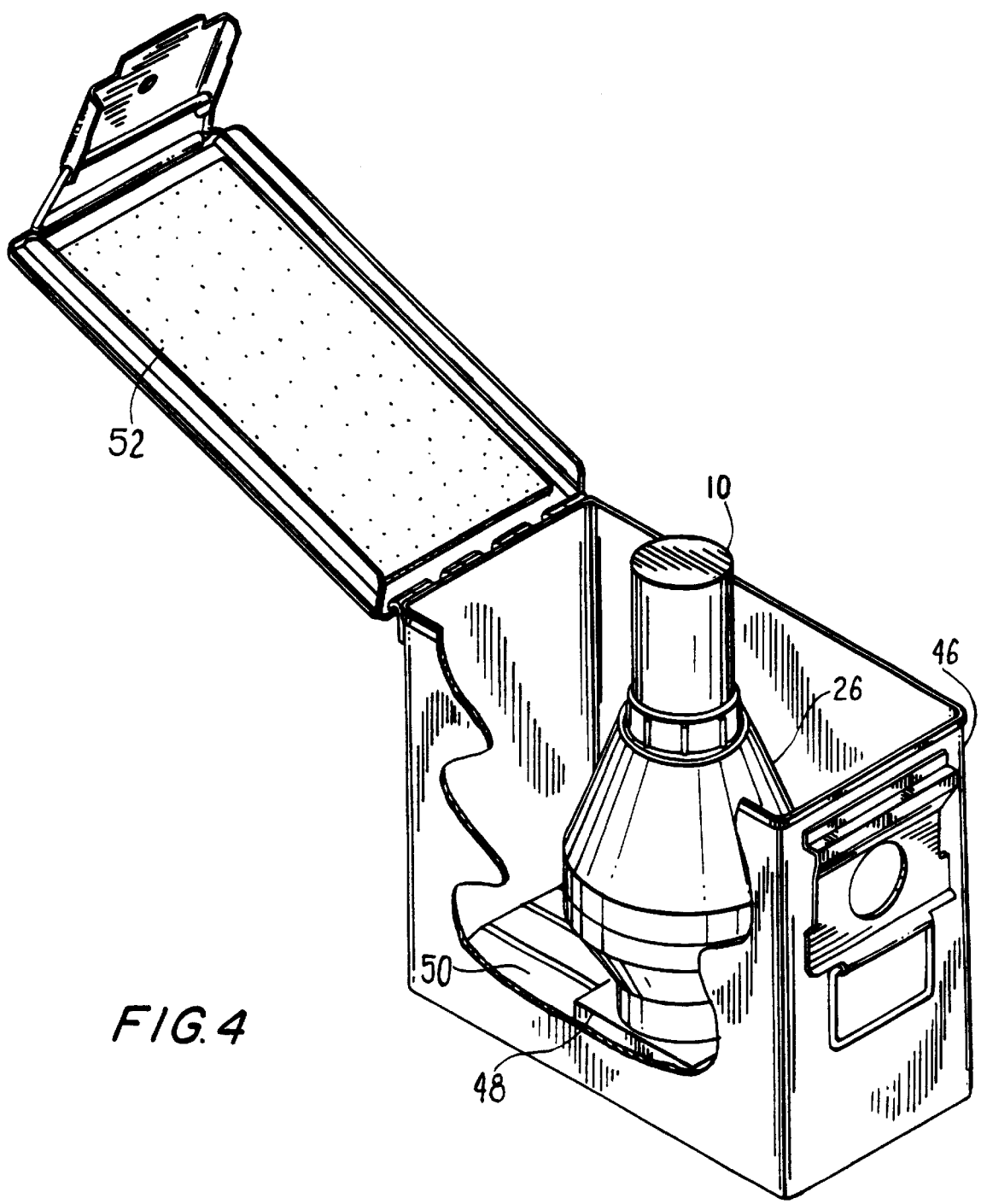
FIG. 4 is a perspective view of the shield and pig inside a conventional ammunition can.
Figure 5:
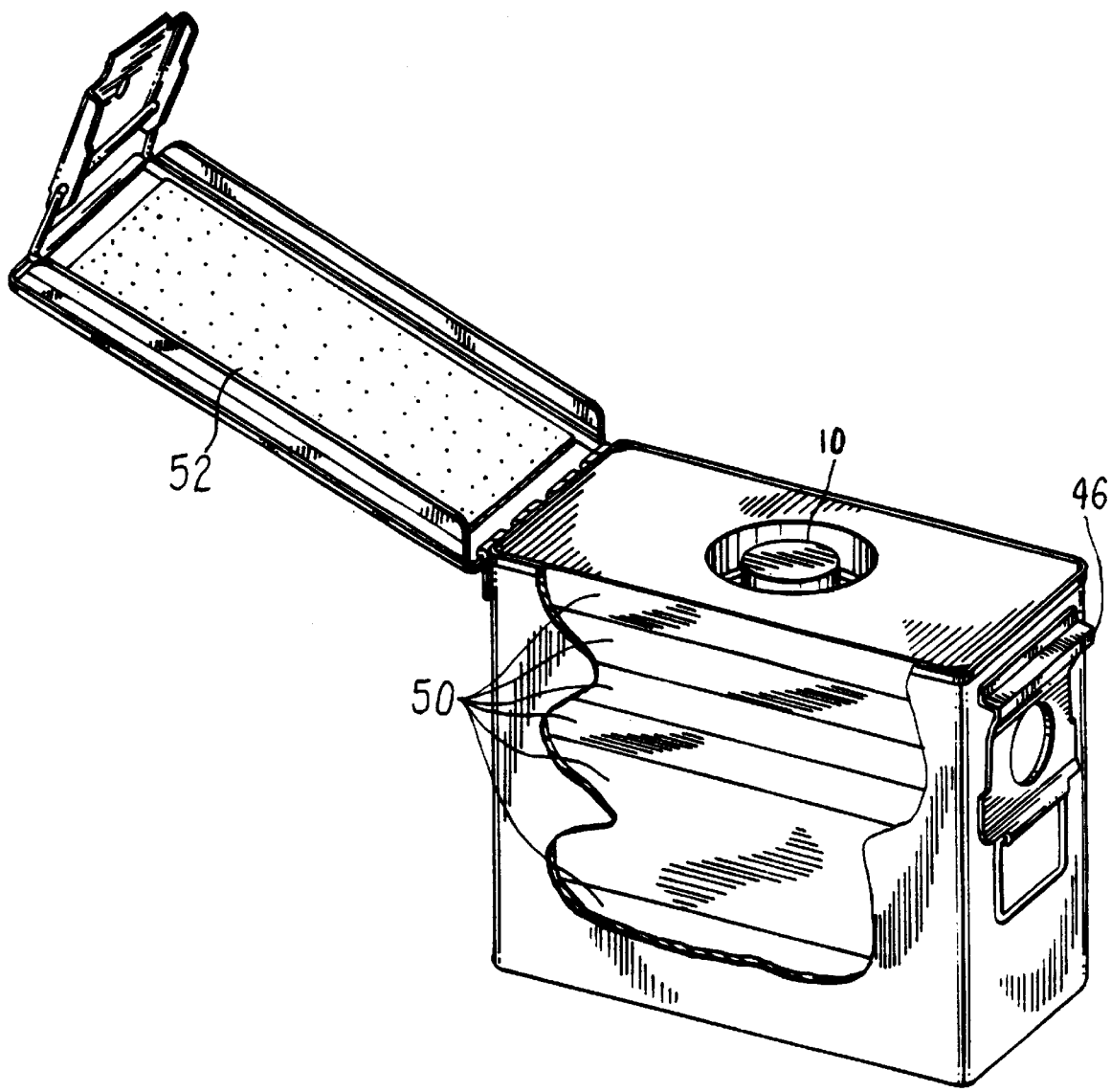
FIG. 5 is an elevational view of the pig and ammunition can.

Turning to FIG. 4, the radiation shield 26 is supported in a shipping container 46 such as a conventional metallic ammunition can or plastic or cardboard container. A sheet metal bracket 48 or some other sufficiently rigid bracket material 48 may be affixed to an inside surface in the case of the container 46 can and held in place with high density foam 50 (FIG. 5), such as high density polyurethane or polyethylene foam. Additional foam 50 between the base 56 of the container 46 (FIG. 1) and a lid 54 clamp the pig 10 in place upon fastening the lid 54 of the container 46.

As shown in FIG. 1, radiation shield 26 is configured to define a cavity 24 into which the pig 10 is arranged. In the preferred embodiment, the radiation shield 26 has a contour that converges toward each of the open ends 28, providing a central area 56 between the two ends that is thicker than the area of the radiation shield 26 proximate to each of the ends. This configuration provides sufficient shielding while minimizing weight. Those skilled in the art will recognize that while the radiation shield 26 illustrated is contoured at both ends, only one end could be contoured, only part of one end could be contoured, the contour could be smaller, it could be arcuate rather than flat, etc. So long as the shape makes the weight less than a full cylindrical shape but maintains sufficient radiation shielding it will still fall within the scope of the invention.

This highly efficient use of the radiation shield 26 allows for the adequate shielding of a FDG F18 dose as high as 700 mCi in containers that weigh less than 50 lbs. and still have a removable pig 10. A different, lighter weight, radiation shield 26 can be used for smaller doses by modifying the radiation shield 26, shown in FIG. 1, to have less lead to create an even lighter shipping container. This saves shipping charges and may also reduce the risk of injury to the people handling the containers as compared to conventional arrangements.

According to DOT regulations, the radioactivity reading on the surface of the shipping container must be less than 50 mRems/hour and must also be less than about 1 mRems/hour at a reading that is taken at a distance of about 1 meter from the shipping container. The amount of lead required for adequate shielding is based on conventional formulae and tables that take into account the pharmaceutical properties, shielding material and distance between the radioactive substance and the outside of the shipping container. The required amount of shielding material drops off rapidly as the distance to the outside of the container increases.

Figure 6:
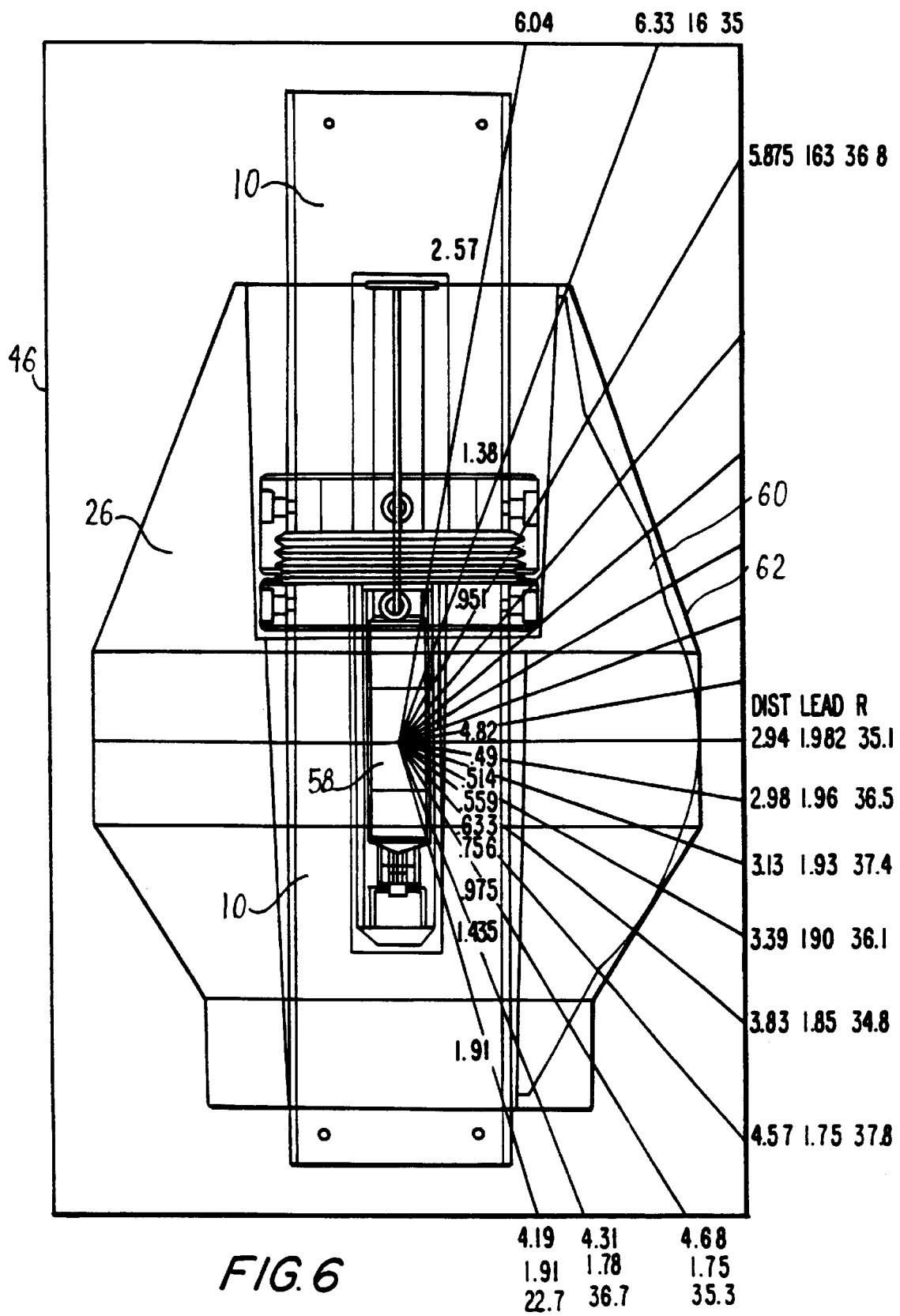
FIG. 6 is a profile diagram indicating the minimum amounts of lead required in the radiation lead shield at particular angles as a function of distance between the radioactive source and the outside of the ammunition can.

FIG. 6 shows the minimum profile for the amount of lead required in the radiation shield 26. The distance between the center of the syringe 32 to the outside of the shipping container 46 along the angles shown is in inches or centimeters. The thickness of lead required for proper shielding, at specific Rems per hour (R), is shown in inches at various angles. The numbers that appear in FIG. 6 near the center thereof show various required thicknesses of the lead forming the pig 10 of the present invention, in inches, for the angles shown. The distances from the radioactive substance to the outside of the shipping container 46 at the angles 58 shown and the thickness of lead in the pig 10 in inches are used to determine the thickness requirements of the radiation shield 26 at the particular angles. The thicknesses are plotted along the angle lines. These points are connected to show the minimum profile 60 of the lead radiation shield. The profile is then modified into a shape 62 that can be manufactured and supported by the shipping container 46.

The minimum amount of lead required in the closed end portions of the pig is dependent upon the activity of the dose being shipped and the distance from the center of the radiopharmaceutical substance to the outside of the shipping container 46. For a dosage of 700 mCi, the end portions of the pig 10 near the lid 52 in the container 46 requires about 1 9/16" lead and the other end portion requires about 1 7/8" lead. If 150 mCi are to be shipped, then about 1.20" lead and 1.39" lead would be required, respectively.

Figure 7:
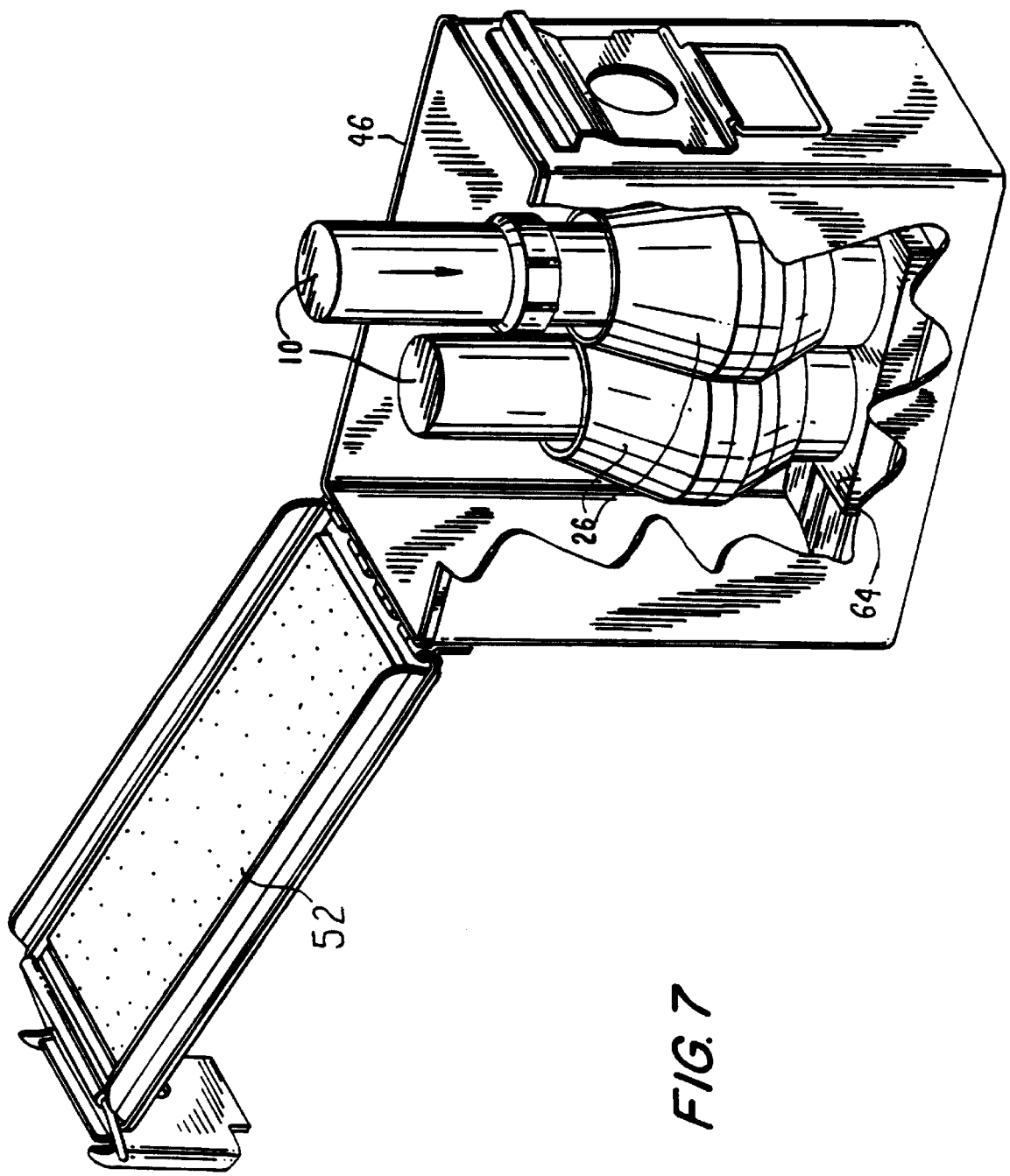
FIG. 7 is a perspective view of an alternate embodiment of the radiopharmaceutical pig and transportation apparatus with a partial cut away of the ammunition can.

FIG. 7 shows another embodiment of the invention for shipping multiple doses of radioactive substances in a single shipping container 46. FIG. 7 shows two individual pigs 10 each placed inside a respective radiation shield 26 configured to accommodate the two pigs 10. The double radiation shield 26 defines two cavities into which are arranged the two pigs 10 wherein the double radiation shield 26 and pigs 10 limit an amount of radioactivity emanating from the radioactive substances and penetrating the pigs 10 and shield 26 to less than about 50 mRems/hour at the surface of the container 46. This embodiment is particularly convenient for nuclear medical facilities that perform multiple PET imaging studies in a single day. The initial strength of each dose depends on the distance between the facility and on the duration of the multiple image studies.

The double radiation shield 26 is supported by a sheet metal bracket 64 or some other suitable material, which may be placed inside a conventional container 46, configured to support the two pigs 10. High density foam 66, as described in connection with the first embodiment of the present invention, is used to keep the pigs 10 in place inside the container 46. Both pigs 10 and the double radiation shield 26 can fit into a standard ammunition can and still weigh less than about 50 lbs.

Figure 8:
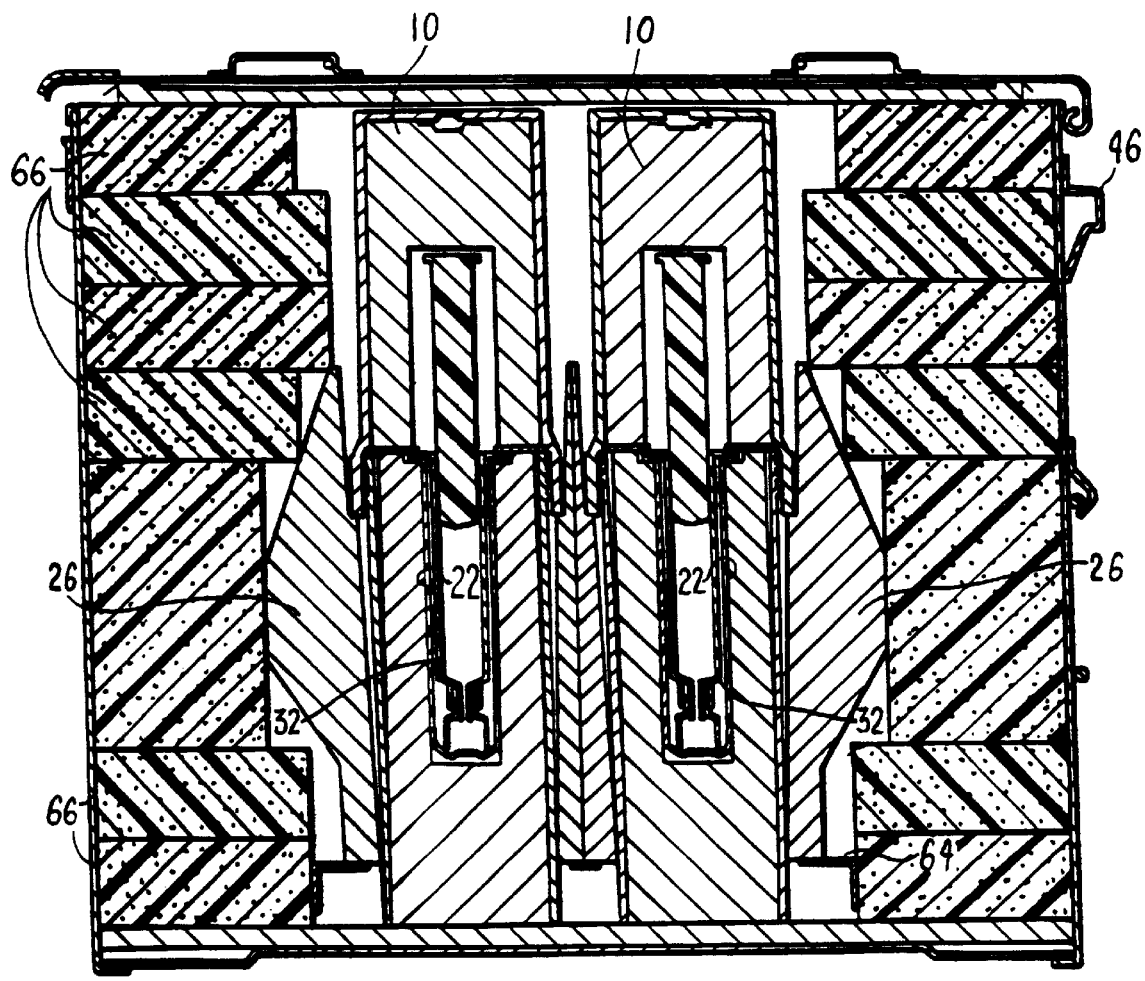
FIG. 8 is a cross section view of the embodiment of FIG. 7.

FIG. 8 shows the syringes 32 and plastic liners used in a second embodiment of the present invention. Each syringe 32 is placed into its own pig 10. Each dose of radiation substance in each of the syringes 32 contains up to 150 mCi. The pigs 10 which now contain the two syringes 32 with their corresponding single doses of radiation substances are then placed into a double radiation shield 26 configured to accommodate the two pigs 10. High density foam 66 keeps the pigs 10 in place against moving inside the container 46.

Although the above describes particular embodiments of the invention, many other variations and modifications and other uses may become apparent to those skilled in the art. It is preferred, that the present invention not be limited by this specific disclosure herein, but only by the appended claims.

What is claimed is:

1. A radiopharmaceutical transportation apparatus comprising:
   a radiation shielding pig having an elongated sidewall that extends between two closed ends and defines an elongated, interior chamber, the sidewall being thinner than each of the closed ends; and
   a radiation shield, having a length and a width, that defines a cavity, at least a portion of the radiation shielding pig being capable of fitting within the cavity, the radiation shield having an open end having an open end width, another end opposite said open end having another end width and a central area between the two ends, wherein said central area has a width that is wider than one of said end widths.

2. The apparatus according to claim 1 wherein said another end is also open.

3. The apparatus according to claim 1 wherein said central area width is wider than both end widths.

4. The apparatus according to claim 1, further comprising a syringe containing a radioactive substance, the syringe being situated within the chamber of the pig.

5. The apparatus according to claim 1, wherein at least one of the pig and the shield are comprised of a radiation penetration resistant material selected from a group consisting of elemental lead, tungsten and steel.

6. The apparatus according to claim 1, wherein the pig has an outer shell selected from at least one of a plastic and a metal.

7. The apparatus according to claim 1, wherein the pig is configured in two selectively mateable sections.

8. The apparatus according to claim 7, wherein the two mateable sections are threaded.

9. The apparatus of claim 1, wherein the radiation shield further comprises a contour that converges toward each of the two open ends from the central area.

10. The apparatus according to claim 1, wherein the cavity is configured to accommodate a plurality of radiation resistant pigs, each pig being selectively situated within the cavity of the shield.

11. The apparatus according to claim 1, further comprising a container into which are placed the pig and the shield and wherein a weight of the pig, the shield and the container is at most about fifty pounds.

12. The apparatus according to claim 1, further comprising a container into which are placed the pig and the shield.

13. The apparatus according to claim 12, wherein foam selected from at least one of high density polyurethane foam and high density polyethylene foam is used to secure the pig and shield within said container in their relative positions with respect to each other.

14. The apparatus according to claim 12, further comprising a bracket arranged and configured to support the radiation shield in the ammunition can.

15. The apparatus according to claim 1, wherein the closed ends of the radiation shielding pig protrude beyond both of the ends of said radiation shield simultaneously.

16. The apparatus according to claim 2 further comprising a sheath configured to fit within said interior chamber of said pig and to receive said syringe.

17. A method of assembling a radiation shielding pig comprising:

placing a syringe with a radiopharmaceutical substance that emits a defined amount of radioactivity into a pig, said pig having an elongated sidewall that extends between two closed ends and defines an elongated interior chamber, the sidewall being thinner than each of the two closed ends;

placing the radioactive shielding pig containing the filled syringe into a cavity of a radiation shield, at least a portion of the radiation shielding pig being within the cavity, the radiation shield having an open end having a width, another end opposite said open end and having another end width, and a central area, having a central area width, between the two ends, the central area width being greater than the width of one of the ends.

18. The method according to claim 17, further comprising:

placing the pig and the shield into a container; and, fastening the container for transporting the radioactive substance contained in the syringe.

19. The method according to claim 17, further comprising extending the closed ends of the pig to protrude through each of the ends of the shield.

20. A method of disassembling a radiopharmaceutical transportation apparatus comprising:

unfastening a container that houses a radiation shielding pig, said pig having an elongated sidewall that extends between two closed ends and that defines an elongated, interior chamber into which a syringe containing a radioactive substance is situated, the sidewall being thinner than each of the two closed ends; and removing the pig from a cavity of a radiation shield, at least a portion of the radiation shielding pig being within the cavity, the radiation shield having two open ends and a central area between the two open ends, the central area being thicker than each of the two open ends.

21. A method of transporting a radiopharmaceutical transportation apparatus comprising:

transporting a container from a first location to a distal location, said container housing a radiation shielding pig, having an elongated sidewall that extends between two closed ends and defines an elongated interior chamber, the sidewall being thinner than each of the two closed ends;

said container also housing a radiation shield having a cavity and into whose cavity the pig is placed, said cavity extending between two open ends such that the two closed ends of the radiation shielding pig protrude beyond both of the open ends of said radiation shield simultaneously.

* * * * *